United States Patent
Zhu et al.

(10) Patent No.: US 10,000,437 B2
(45) Date of Patent: Jun. 19, 2018

(54) NITROGEN CONTAINING SURFACTANTS WITH ALKOXYLATION ON THE HYDROXYL GROUP OF FATTY CHAINS

(71) Applicant: Akzo Nobel Chemicals International B.V., Amersfoort (NL)

(72) Inventors: Shawn Zhu, Stormville, NY (US); Biing-Ming Su, Croton-on-Hudson, NY (US); Giao Vinh Nguyen, Friendswood, TX (US); Louis Schwarzmayr, Hjälteby (SE); Jinxia Susan Sun, Hopewell Junction, NY (US); Xiaoyu Wang, Shanghai (CN); Elliot Isaac Band, Pleasantville, NY (US); Mojahedul Islam, White House Station, NY (US); Christine Puglisi, Mountainside, NJ (US); Wyatt Winkenwerder, New Milford, CT (US); Charles Woodville Davis, Houston, TX (US)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days. days.

(21) Appl. No.: 14/770,524

(22) PCT Filed: Mar. 13, 2014

(86) PCT No.: PCT/EP2014/055017
§ 371 (c)(1),
(2) Date: Aug. 26, 2015

(87) PCT Pub. No.: WO2014/140214
PCT Pub. Date: Sep. 18, 2014

(65) Prior Publication Data
US 2016/0009627 A1    Jan. 14, 2016

Related U.S. Application Data

(60) Provisional application No. 61/782,473, filed on Mar. 14, 2013.

(30) Foreign Application Priority Data

Jul. 3, 2013 (EP) .................................... 13174883

(51) Int. Cl.
*C07C 59/305* (2006.01)
*A01N 25/30* (2006.01)
(Continued)

(52) U.S. Cl.
CPC ............ *C07C 59/305* (2013.01); *A01N 25/30* (2013.01); *A01N 37/36* (2013.01); *A01N 37/40* (2013.01);
(Continued)

(58) Field of Classification Search
CPC .. A61K 2300/00; A61K 31/165; A61K 31/18; A61K 31/235; A61K 31/24;
(Continued)

(56) References Cited

U.S. PATENT DOCUMENTS 2,542,550 A    2/1951 McDermott
3,312,542 A    4/1967 Kitzke et al.
(Continued)

FOREIGN PATENT DOCUMENTS

EP    0992488 A2 *  9/1999 ........... C07C 235/10
EP    0992488 A2    4/2000
(Continued)

OTHER PUBLICATIONS

International Search Report and Written Opinion for PCT/EP2014/055017, dated Aug. 11, 2014.
European Search Report for 13174883.2, dated Oct. 29, 2013.
Mihail Ionescu et al., Ethoxylated Soybean Polyols for Polyurethanes, J. Polym Environ, vol. 15, Oct. 11, 2007 (Oct. 11, 2007), pp. 237-243, XP002714299, Springer.

*Primary Examiner* — Audrea Buckley
(74) *Attorney, Agent, or Firm* — McDonnell Boehnen Hulbert & Berghoff LLP

(57) ABSTRACT

The present invention is directed to a nitrogen containing surfactant composition comprising at least one nitrogen containing surfactant of structure (h) or structure (i). The nitrogen containing surfactant of structure (h) is as shown below: Structure (h). The nitrogen containing surfactant of structure (i) is as shown below: Structure (i). The present invention is also directed to an agricultural composition comprising at least one agrochemical and at least one nitrogen containing surfactant composition of the present invention.

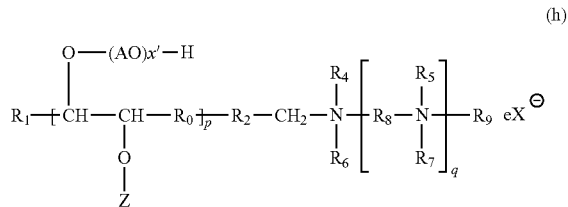

(h)

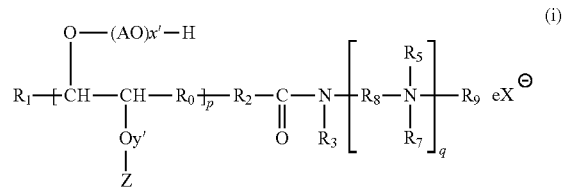

(i)

36 Claims, 2 Drawing Sheets

(51) Int. Cl.

| | | |
|---|---|---|
| *C07C 235/10* | (2006.01) | |
| *A01N 37/36* | (2006.01) | |
| *C07C 235/00* | (2006.01) | |
| *C11D 1/40* | (2006.01) | |
| *C11D 1/42* | (2006.01) | |
| *C11D 1/44* | (2006.01) | |
| *C11D 1/52* | (2006.01) | |
| *A01N 37/40* | (2006.01) | |
| *A01N 39/04* | (2006.01) | |
| *A01N 57/20* | (2006.01) | |
| *C07C 51/02* | (2006.01) | |

(52) U.S. Cl.
CPC ............ *A01N 39/04* (2013.01); *A01N 57/20* (2013.01); *C07C 51/02* (2013.01); *C07C 235/00* (2013.01); *C07C 235/10* (2013.01); *C11D 1/40* (2013.01); *C11D 1/42* (2013.01); *C11D 1/44* (2013.01); *C11D 1/52* (2013.01)

(58) Field of Classification Search
CPC .. A61K 31/405; A61K 31/425; A61K 31/426; A61K 31/43; A61K 31/545; A61K 45/06; A01N 2300/00; A01N 57/16; A01N 61/00; A01N 25/32; A01N 37/10; A01N 37/22; A01N 37/28; A01N 37/30; A01N 37/38; A01N 37/46; A01N 41/06; A01N 43/12; A01N 43/16; A01N 43/38; A01N 43/40; A01N 43/78; A01N 47/06; A01N 47/30; A01N 47/44
See application file for complete search history.

(56) References Cited

U.S. PATENT DOCUMENTS

| | | |
|---|---|---|
| 4,220,581 A | 9/1980 | Cooperman et al. |
| 2006/0276339 A1* | 12/2006 | Windsor ............... A01N 25/32 504/127 |

FOREIGN PATENT DOCUMENTS

| | | |
|---|---|---|
| JP | 10-167915 A | 6/1998 |
| JP | 2003-535056 A | 11/2003 |
| WO | 01/89302 A2 | 11/2001 |
| WO | 2012/059156 A1 | 5/2012 |

\* cited by examiner

Figure 1. Bioefficacy enhancing effect of novel castor oil ethoxylate derivatives on wheat

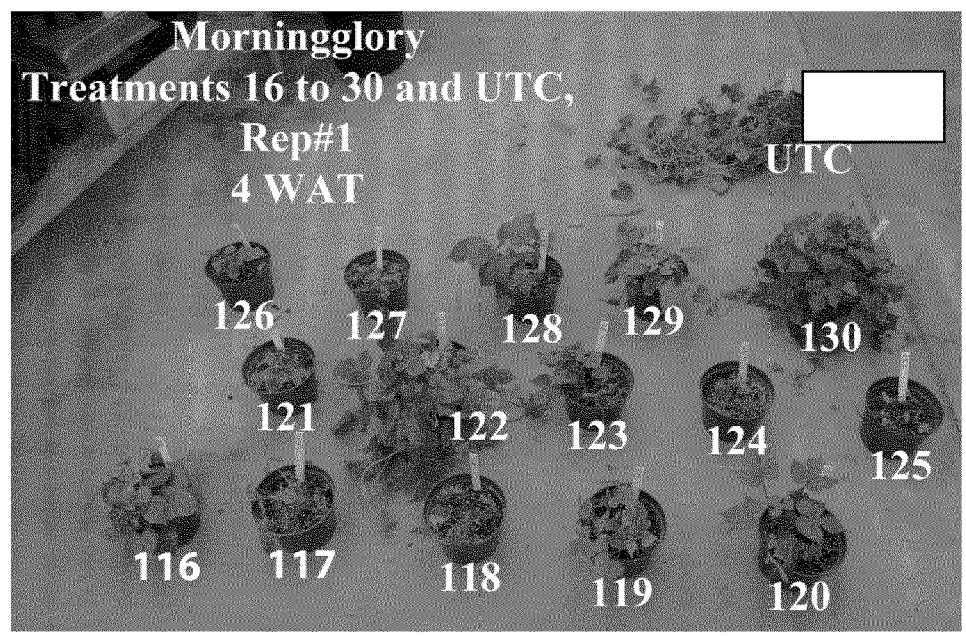
Figure 2. Bioefficacy enhancing effect of novel castor oil ethoxylate derivatives on morning glory

NITROGEN CONTAINING SURFACTANTS WITH ALKOXYLATION ON THE HYDROXYL GROUP OF FATTY CHAINS

This application is a national stage filing under 35 U.S.C. § 371 of PCT/EP2014/055017, filed Mar. 13, 2014, which claims priority to U.S. Provisional Patent Application No. 61/782,473 filed Mar. 14, 2013, and European Patent Application No. 13174883.2, filed Jul. 3, 2013, the contents of which are each incorporated herein by reference in their entireties.

FIELD OF THE INVENTION

The present invention relates to a nitrogen containing surfactant composition useful in agricultural formulations. The present invention also relates to methods of making the nitrogen containing surfactant composition.

BACKGROUND OF THE INVENTION

Alkoxylated nitrogen containing surfactants such as tallowamine ethoxylate and its quaternary surfactants find use as an adjuvant capable of enhancing pesticide activities. The most well-known application of tallowamine ethoxylate and its quaternary surfactants is to enhance glyphosate efficacy. In a typical tallowamine alkoxylate, the alkoxylation occurs on the nitrogen atom.

There has no prior art disclosing the use of a nitrogen containing surfactant with alkoxylation on the pendant (or secondary) hydroxyl group on the hydrocarbon chain.

Typically, in the alkoxylation of hydroxyl compound using an alkaline (OH⁻) as a catalyst, a polyalkylene oxide (PAO) chain is attached to the hydroxyl group. However, in the alkoxylation of triglycerides with pendant hydroxyl group, the great majority of the PAO chains are inserted to the ester group meanwhile only a minute portion of the PAO chains are attached to the hydroxyl group. The conventional alkoxylation reaction with an alkaline catalyst may be illustrated as shown in the following reaction (I):

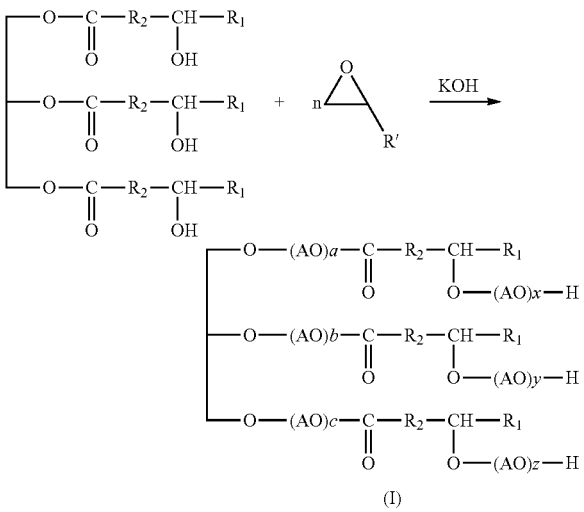

where $R_1$ and $R_2$ each have 5-16 carbons, saturated or unsaturated, linear or branched alkyl groups; A is a C2-C3 alkylene; a, b, c, x, y and z each is equal or greater than 0; a+b+c+x+y+z=n. The reaction at the hydroxyl groups is minor, i.e., a+b+c>>x+y+z.

When a fatty acid (or ester) is used instead of the triglyceride, an ethoxylation reaction can be similarly illustrated as shown in the following reaction (II):

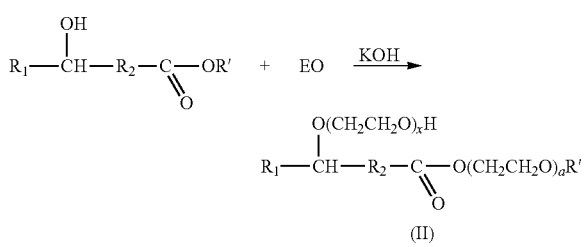

where R' is H or methyl (or higher alkyl), $R_1$, $R_2$, x, and a are defined as in reaction (I) previously, and a>>x.

Non-limiting examples of fatty acids with a pendant hydroxyl group are castor acid and epoxidized soy acid.

Using ethoxylation of castor oil as an example, if the ethoxylation reaction of the castor oil is run using a Lewis acid, such as BF3 as catalyst, a surfactant is created in which the ethoxylation (EO) units were selectively attached to the OH groups on the fatty chain rather than inserted to the ester groups in the castor oil as it typically occurs with conventional alkaline catalyst process. That is, in reaction products in reactions (1), x, y and z each=0 to 7; a, b, or c is an integer of zero or more; x+y+z is more than about 95% of a+b+c+x+y+z. Similarly, in reaction products in reactions (II), x=0 to 7; a is an integer of zero or more; x is more than about 95% of a+x.

The selective ethoxylation attachment process can also be used for fatty acids, fatty acid esters, monoglycerides, and diglycerides. The selective attachment of PAO to the OH group can be confirmed by NMR analyses.

Using $BF_3$ as catalyst, if more than ~7 EO (per alkyl chain, i.e. x, y or z) is added, too much undesirable side product (dioxane) will be generated. However, if desired, more EO can be added subsequently by using KOH as catalyst without generating additional dioxane. When using KOH as catalyst, additional EO added will be both attached to the pendant ethoxylated groups and inserted to the ester groups. If one assumes equal reactivity, additional EO's will be equally distributed between attachment and insertion.

It should be noted that with regard to the PAO numbers in an alkoxylate, the PAO numbers of a, b, c, x, y, and z are average numbers. One skilled in the art understands that this is due to the nature of alkoxylation polymerization. For example, when x is 5, it means that the average PAO distribution is 5 PAO units on a particular hydrocarbon chain. Some molecules in the product may have zero PAO at the x position while some may have 12 PAO units at the x position.

SUMMARY OF THE INVENTION

The present invention is directed to a nitrogen containing surfactant derived from the triglycerides, fatty acids, or methylester of fatty acids where the triglycerides, fatty acids, or methylester of fatty acids has at least one pendant hydroxyl group on the hydrocarbon chain. The pendant hydroxyl group may be alkoxylated.

The nitrogen containing surfactant composition of the present invention comprises at least one nitrogen containing surfactant of structure (h) or structure (i). The nitrogen containing surfactant of structure (h) is as shown below:

Structure (h)

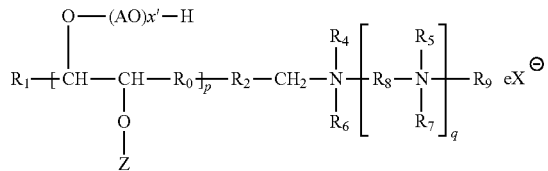

wherein p is 1-3; $R_0$ is nothing or C1-C6 alkylene; $R_1$ and $R_2$ each independently are C1-18 hydrocarbons, saturated or unsaturated, linear or branched alkyl or alkylene groups so that the total hydrocarbon chain length is C14 to C22; A is a C2-C3 alkylene; x' is 0-100; Z is C1-C22 alkyl or a polyalkylene oxide $(A'O)_{w'}H$ where A' is a C2-C3 alkylene and w' is 0-100; $R_4$, $R_5$, $R_6$, $R_7$, and $R_9$ are the same or different and are selected from nothing, H, $CH_3$, $CH_3CH_2$, $(A''O)_wH$ where A'' is a C2-C3 alkylene and w=1-100, O (oxygen), $CH_2$—COO, $CH_2$—$COO^-M^+$, $CH_2$—$CH_2$—$COO^-M^+$, $CH_2$—$CH_2$—$CH_2$—$SO_3$, or $CH_2$—CH(OH)—$CH_2$—$SO_3$; q=0-5; $R_8$ is C2-C3 alkylene; $X^-$ is an anion and e is a value that balances the charge in the molecule when N is a quaternary nitrogen; and $M^+$ is a suitable cation.

The nitrogen containing surfactant of structure (i) is as shown below:

Structure (i)

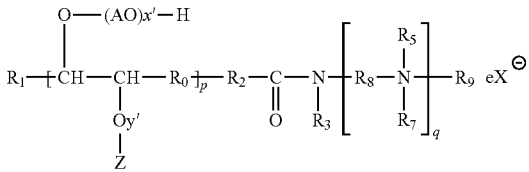

wherein p is 1-3; $R_0$ is nothing or C1-C6 alkylene; $R_1$ and $R_2$ each independently are C1-18 hydrocarbons, saturated or unsaturated, linear or branched alkyl or alkylene groups so that the total hydrocarbon chain length is C14 to C22; A is a C2-C3 alkylene; x' is 0-100; y' is 0 or 1; Z is a H (hydrogen) when y'=0, a C1-C22 alkyl when y'=1, or a polyalkylene oxide $(A'O)_{w'}H$ when y'=1 where A' is a C2-C3 alkylene and w' is 0-100; R3 is H, $CH_3$, or $(A'''O)_{w'}H$ where A''' is a C2-C3 alkylene and w''=1-100; R5, R7, and R9 are the same or different and are selected from nothing, H, $CH_3$, $CH_3CH_2$, $(A''O)_wH$ where A'' is a C2-C3 alkylene and w=1-100, O (oxygen), $CH_2$—COO, $CH_2$—$COO^-M^+$, $CH_2$—$CH_2$—$COO^-M^+$, $CH_2$—$CH_2$—$CH_2$—$SO_3$, or $CH_2$—CH(OH)—$CH_2$—$SO_3$; q=1-5; R8 is C2-C3 alkylene; $X^-$ is an anion and e is a value that balances the charge in the molecule when N is a quaternary nitrogen; and $M^+$ is a suitable cation.

Furthermore, the present invention is directed to an agro composition comprising at least one agrochemical and at least one nitrogen containing surfactant of structure (h) or (i).

Lastly, the present invention is also directed to methods of making the nitrogen containing surfactant with structures (h) and (i).

BRIEF DESCRIPTION OF THE DRAWINGS

FIG. 1 shows the bioefficacy enhancing effect of the castor oil ethoxylate derivatives according to the present invention on wheat.

FIG. 2 shows the bioefficacy enhancing effect of the castor oil ethoxylate derivatives on morning glory.

DETAILED DESCRIPTION OF THE INVENTION

The present invention is directed to a nitrogen containing surfactant derived from the triglycerides, fatty acids, or methylester of fatty acids where the triglycerides, fatty acids, or methylester of fatty acids has at least one pendant hydroxyl group on the hydrocarbon chain. The pendant hydroxyl group may be alkoxylated.

The nitrogen containing surfactant composition of the present invention comprises at least one nitrogen containing surfactant of structure (h) or structure (i). The nitrogen containing surfactant of structure (h) is as shown below:

Structure (h)

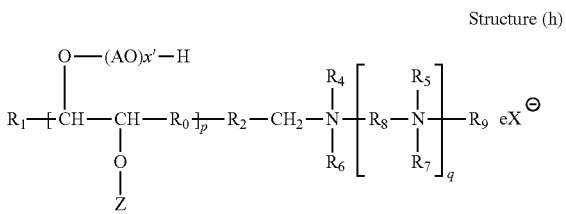

wherein p is 1-3; $R_0$ is nothing or C1-C6 alkylene, preferably nothing or C1 alkylene; $R_1$ and $R_2$ each independently are C1-C18, preferably C1-C14 hydrocarbons, saturated or unsaturated, linear or branched alkyl or alkylene groups so that the total hydrocarbon chain length is C14 to C22, preferably C16-C18; A is a C2-C3 alkylene; x' is 0-100, preferably 1-100, more preferably 1-50, even more preferably 5-20; Z is C1-C22, preferably C1-C18 alkyl or a polyalkylene oxide $(A'O)_{w'}H$ where A' is a C2-C3 alkylene and w' is 0-100, preferably 1-50, more preferably 5-20; $R_4$, $R_5$, $R_6$, $R_7$, and $R_9$ are the same or different and are selected from nothing, H, $CH_3$, $CH_3CH_2$, $(A''O)_wH$ where A'' is a C2-C3 alkylene and w=1-100, preferably 1-50, more preferably 5-20, O (oxygen), $CH_2$—COO, $CH_2$—$COO^-M^+$, $CH_2$—$CH_2$—$COO^-M^+$, $CH_2$—$CH_2$—$CH_2$—$SO_3$, or $CH_2$—CH(OH)—$CH_2$—$SO_3$; q=0-5, preferably 0-3; $R_8$ is C2-C3 alkylene; $X^-$ is an anion and e is a value that balances the charge in the molecule when N is a quaternary nitrogen; and M is a suitable cation.

The nitrogen containing surfactant of structure (h) is as shown below:

Structure (i)

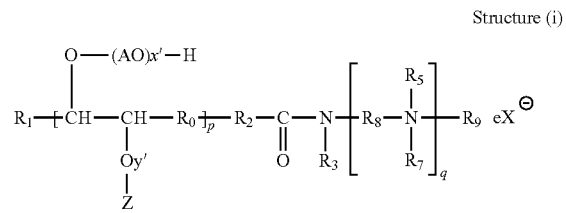

wherein p is 1-3; $R_0$ is nothing or C1-C6 alkylene, preferably nothing or C1 alkylene; $R_1$ and $R_2$ each independently are C1-C18, preferably C1-C14 hydrocarbons, saturated or unsaturated, linear or branched alkyl or alkylene groups so that the total hydrocarbon chain length is C14 to C22, preferably C16-C18; A is a C2-C3 alkylene; x' is 0-100, preferably 1-100, more preferably 1-50, even more preferably 5-20; y' is 0 or 1; Z is a H (hydrogen) when y'=0, a C1-C22 alkyl when y'=1, or a polyalkylene oxide $(A'O)_{w'}H$ when y'=1 where A' is a C2-C3 alkylene and w' is 0-100, preferably 1-50, more preferably 5-20; R3 is H, $CH_3$, or $(A'''O)_{w'''}H$ where A''' is a C2-C3 alkylene and w'''=1-100, preferably 1-50, more preferably 5-20; R5, R7, and R9 are the same or different and are selected from nothing, H, $CH_3$, $CH_3CH_2$, $(A''O)_{w}H$ where A'' is a C2-C3 alkylene and w=1-100, preferably 1-50, more preferably 5-20, O (oxygen), $CH_2$—COO, $CH_2$—$COO^-M^+$, $CH_2$—$CH_2$—$COO^-$$M^+$, $CH_2$—$CH_2$—$CH_2$—$SO_3$, or $CH_2$—CH(OH)—$CH_2$—$SO_3$; q=1-5, preferably 1-3; R8 is C2-C3 alkylene; $X^-$ is an anion and e is a value that balances the charge in the molecule when N is a quaternary nitrogen; and $M^+$ is a suitable cation.

The surfactants with structure (h) may be prepared using the method illustrated as follows:

1. Amination—Reaction of unsaturated fatty acid with ammonium to make fatty nitrile, a well-known process:

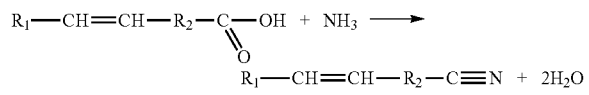

where $R_1$, $R_2$ are defined previously in structure (h).

2. Epoxidize the fatty nitrile of Step 1, a well-known process:

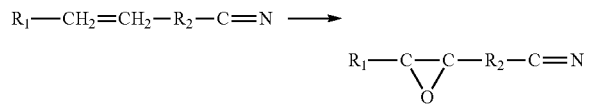

3. Ring open reaction of the product of Step 2:

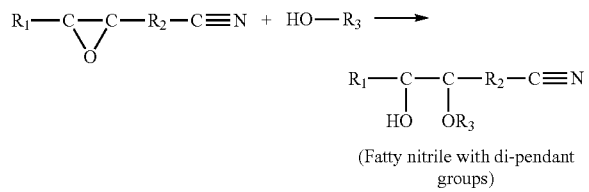

(Fatty nitrile with di-pendant groups)

where $R_3$ is alkyl, or $(AO)_wH$ where w is 0-100, preferably 1-50, and A is C2-C3 alkyl.

4. Ethoxylate the nitrile with di-pendant groups of Step 3 and obtain the following ethoxylated fatty nitrile (as disclosed in WO01/00567, which is incorporated herein by reference in its entirety):

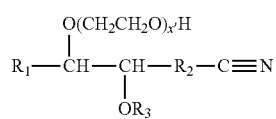

where x' is 0-100, preferably 1-100, more preferably 1-50, even more preferably 5-20; $R_3$ is alkyl, or $(A'O)_{w'}H$ where w' is 0-100, preferably 1-100, more preferably 1-50, even more preferably 5-20, and A' is C2-C3 alkyl.

5. Reduction of the ethoxylated fatty nitrile of Step 4 to obtain the following ethoxylated fatty primary amine:

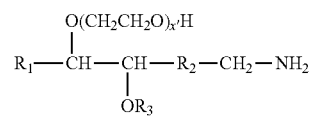

6. The ethoxylated fatty primary amine of Step 5 can be further ethoxylated to produce tertiary fatty amine ethoxylate, which can be used further to make amine oxide and quaternary with well-known processes.

7. The ethoxylated fatty primary amine of Step 5 can be further made into polyamine by acrylonitrile process, followed by ethoxylation.

8. The ethoxylated fatty primary amine of Step 5 can be further reacted with Cl-$CH_2$—COONa to obtain

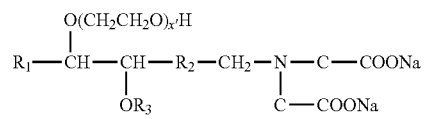

9. The ethoxylated fatty primary amine of Step 5 can be further reacted with CH2=CHCOOH to obtain

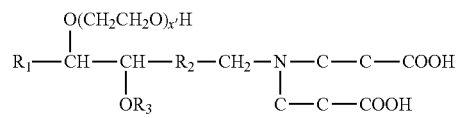

It is understood that while each step above may be a known process, the combination of the steps is believed to be novel and inventive.

The surfactants with structure (i) may be prepared using the method illustrated as follows:

(a) Ethoxylation of fatty acid, fatty ester, or triglyceride with pendant hydroxyl groups to obtained ethoxylated product:

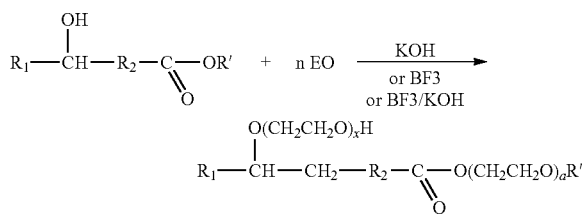

where $R_1$ and $R_2$ are defined previously in structure (i); R' is H or alkyl (preferably methyl); a and x is each 0-100, preferably 1-100, more preferably 1-50, even more preferably 5-20; a+x=n. When n is 7 or less, preferred catalyst is $BF_3$.

The ethoxylated product is the basis for making structure (i) which can be obtained by reacting the ethoxylated product with an amine or polyamine.

(b) The ethoxylated product in step (a) can react with various amines, polyamines, and other reactants to obtain the surfactants with structure (i). Non-limiting examples are:

(1)

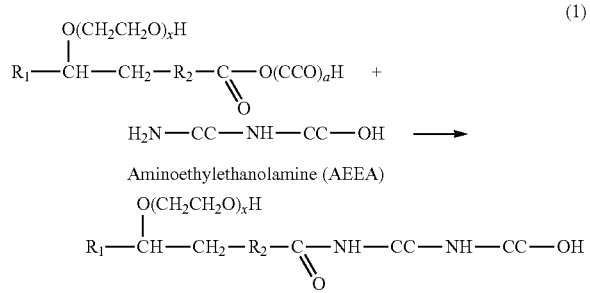

Aminoethylethanolamine (AEEA)

Further ethoxylation can be performed. Further reaction with hydrogen peroxide or methyl chloride can produce amine oxide or quaternary surfactant.

(2)

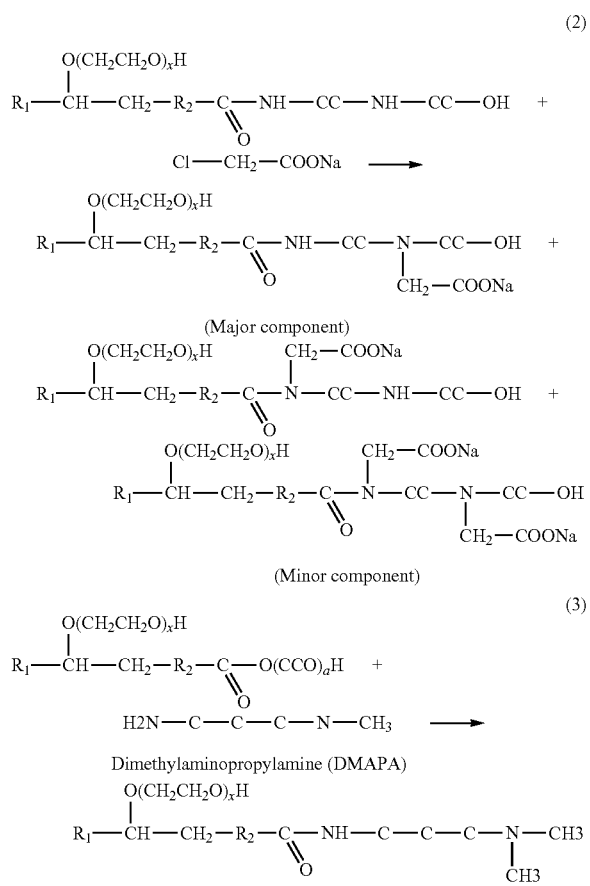

Further ethoxylation can be performed (to increase the pendant EO group). Further reaction with hydrogen peroxide on the tertiary amine, Cl—CH2-COONa, and methyl chloride on the tertiary amine can produce amine oxide, betaine, and quaternary surfactant.

(4)

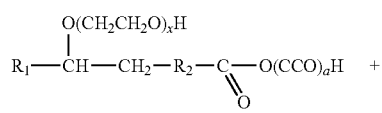

-continued

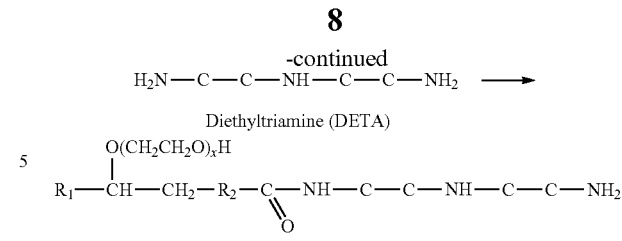

Further reactions with Cl—CH$_2$—COONa or ethylene oxide can be performed, which can be followed by further reaction with hydrogen peroxide or methyl chloride to produce amine oxide or quaternary surfactant.

Similarly, another preferred process of making surfactants with structure (i) is to react epoxidized (or di-pendant) soy methylester (or acid) with an amine and the process is illustrated as follows:

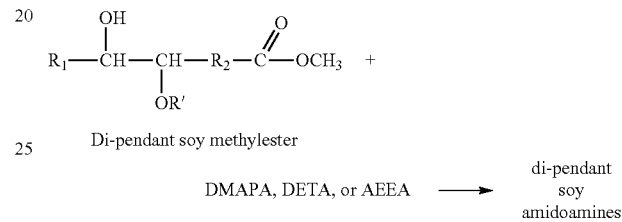

Similarly, the di-pendant amidoamines may further react with Cl—CH$_2$—COONa, CH$_2$=CHCOOH, hydrogen peroxide (on tertiary amine group), methyl chloride (on tertiary amine group), or ethylene (or propylene) oxide, to obtain further derivatives of the present invention.

Other well-known reaction processes, not disclosed here, can be used to obtain other structures in structure (i).

The method of making the nitrogen containing surfactant of structure (i) may be carried out by making the amide or amidoamine first, followed by alkoxylation. The alkoxylation will add alkoxylate to the pendant hydroxyl groups as well as the hydrogen attached to amine nitrogen. Such a method and the nitrogen containing surfactant made with such method are also within the scope of the present invention.

Throughout the context of the present invention, the hydrocarbon is preferably derived from castor oil or epoxidized soy oil (fatty acid, or fatty ester).

In a first embodiment, the nitrogen containing surfactant is the surfactant of structure (h)

Structure (h)

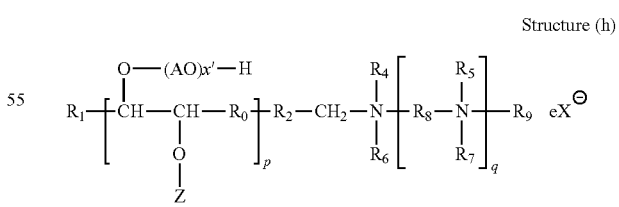

wherein p is 1-3; $R_0$ is nothing or C1-C6 alkylene, preferably nothing or C1 alkylene; $R_1$ and $R_2$ each independently are C1-C18, preferably C1-C14 hydrocarbons, saturated or unsaturated, linear or branched alkyl or alkylene groups so that the total hydrocarbon chain length is C14 to C22, preferably C16-C18; A is a C2-C3 alkylene; x' is 0-100, preferably 1-100, more preferably 1-50, even more preferably 5-20; Z is C1-C22, preferably C1-C18 alkyl or a polyalkylene oxide $(A'O)_{w'}H$ where A' is a C2-C3 alkylene and w' is 0-100, preferably 0-50, more preferably 5-20; $R_4$ and $R_6$ are each methyl; q=0; $R_9$ is nothing; and e is zero.

The second embodiment, the nitrogen containing surfactant is the same as the first embodiment except $R_9$ is $CH_2$—COO.

The third embodiment, the nitrogen containing surfactant is the same as the first embodiment except $R_9$ is O (oxygen).

The fourth embodiment, the nitrogen containing surfactant is the same as the first embodiment except $R_9$ is methyl (or ethyl), e is 1, and X is chloride (or sulfate).

In a fifth embodiment, the nitrogen containing surfactant is the surfactant of structure (h) wherein p, $R_0$, $R_1$, $R_2$, A, x', Z, q, $R_9$, and e are the same as in the first embodiment; $R_4$ and $R_6$ are each $(A"O)_wH$ where A" is a C2-C3 alkylene and w is 1-100, preferably 1-50, more preferably 5-20.

The sixth embodiment, the nitrogen containing surfactant is the same as the fifth embodiment except $R_9$ is O (oxygen).

The seventh embodiment, the nitrogen containing surfactant is the same as the fifth embodiment except $R_9$ is methyl (or ethyl); e is 1; and X is chloride (or sulfate).

The eighth embodiment, the nitrogen containing surfactant is the same as the fifth embodiment except $R_4$ and $R_6$ are each $CH_3$ or $(A"O)_wH$ where A" is a C2-C3 alkylene and w=1, and $R_9$ is C—COO.

In a ninth embodiment, the nitrogen containing surfactant is the surfactant of structure (i)

Structure (i)

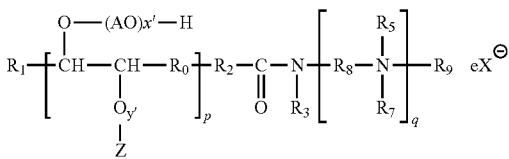

wherein p is 1-3; $R_0$ is nothing or C1-C6 alkylene, preferably nothing or C1 alkylene; $R_1$ and $R_2$ each independently are C1-C18, preferably C1-C14 hydrocarbons, saturated or unsaturated, linear or branched alkyl or alkylene groups so that the total hydrocarbon chain length is C14 to C22, preferably C16-C18; A is a C2-C3 alkylene; x' is 0-100, preferably 1-100, more preferably 1-50, even more preferably 5-20; y' is 0 or 1; Z is a H (hydrogen) when y'=0, a C1-C22, preferably C1-C18 alkyl when y'=1, or a polyalkylene oxide $(A'O)_{w'}H$ when y'=1 where A' is a C2-C3 alkylene and w' is 0-100, preferably 1-50, more preferably 5-20; $R_3$ is H; R5 and R7 are $CH_3$, $R_9$ is nothing, q=1; R8 is C3 propylene; and e is zero.

The tenth embodiment, the nitrogen containing surfactant is the same as the ninth embodiment except $R_9$ is O (oxygen).

The eleventh embodiment, the nitrogen containing surfactant is the same as the ninth embodiment except $R_9$ is C—COO.

The twelfth embodiment, the nitrogen containing surfactant is the same as the ninth embodiment except $R_9$ is methyl (or ethyl), e is 1, and X is chloride (or sulfate).

In a thirteenth embodiment, the nitrogen containing surfactant is the surfactant of structure (i) wherein p, $R_0$, $R_1$, $R_2$, A, x', Z, y', R3, q, $R_9$, and e are the same as in the ninth embodiment, $R_8$ is C2 ethylene, $R_5$ is H, and $R_7$ is $(A"O)_wH$ where A" is a C2-C3 alkylene and w=1.

In a fourteenth embodiment, the nitrogen containing surfactant is the surfactant of structure (i) wherein p, $R_0$, $R_1$, $R_2$, A, x', Z, y', q, $R_9$, and e are the same as in the ninth embodiment; $R_8$ is C2 ethylene; $R_3$ is H or $(A'''O)_{w''}H$ where A''' is a C2-C3 alkylene, w" is 1-100, preferably 1-50, more preferably 5-20; and $R_5$ and $R_7$ is $(A"O)_wH$ where A" is a C2-C3 alkylene, w is 1-100, preferably 1-50, more preferably 5-20.

In a fifteenth embodiment, the nitrogen containing surfactant is the surfactant of structure (i) wherein p, $R_0$, $R_1$, $R_2$, A, x', Z, y', q, and e are the same as in the ninth embodiment; $R_8$ is C2 ethylene; $R_3$ is independently each H or $(A'''O)_{w''}H$ where A''' is a C2-C3 alkylene, w" is 1-100, preferably 1-50, more preferably 5-20; $R_5$ and $R_7$ are $(A"O)_wH$ where A" is a C2-C3 alkylene, w is 1-100, preferably 1-50, more preferably 5-20; and $R_9$ is O (oxygen).

The sixteenth embodiment, the nitrogen containing surfactant is the same as the fifteenth embodiment except R9 is methyl (or ethyl), e is 1, and X is chloride (or sulfate).

In a seventeenth embodiment, the nitrogen containing surfactant is the surfactant of structure (i) wherein p, $R_0$, $R_1$, $R_2$, A, x', Z, y', $R_9$, and e are the same as in the ninth embodiment, $R_8$ is C2 ethylene; q=2; $R_3$ is H or $(A'''O)_{w''}H$ where A''' is a C2-C3 alkylene, w" is 1-100, preferably 1-50, more preferably 5-20; $R_7$ is H or $(A"O)_wH$ where A" is a C2-C3 alkylene, w is 1-100, preferably 1-50, more preferably 5-20; $R_5$ is nothing, H, or $(A"O)_wH$ where A" is a C2-C3 alkylene, w is 1-100, preferably 1-50, more preferably 5-20.

In a eighteenth embodiment, the nitrogen containing surfactant is the surfactant of structure (i) wherein p, $R_0$, $R_1$, $R_2$, A, x', Z, y', and e are the same as in the ninth embodiment; R8 is C2 ethylene; q=2; $R_3$ is H or $(A'''O)_{w''}H$ where A''' is a C2-C3 alkylene, w" is 1-100, preferably 1-50, more preferably 5-20; $R_5$ is nothing or O (oxygen); $R_7$ is $(A"O)_wH$ where A" is a C2-C3 alkylene, w is 1-100, preferably 1-50, more preferably 5-20; and $R_9$ is nothing or O (oxygen).

The nineteenth embodiment, the nitrogen containing surfactant is the same as the eighteenth embodiment except $R_5$ is nothing or $CH_3$; $R_9$ is nothing or $CH_3$ (or ethyl); e is 1 or 2, and X is chloride (or sulfate).

The present invention is also directed to an agricultural composition comprising at least one nitrogen containing surfactant of the present invention and at least one agricultural chemical.

The present invention is further directed to an agricultural composition comprising at least one agricultural chemical and at least one nitrogen containing surfactant composition, the nitrogen containing surfactant composition comprising at least one nitrogen containing surfactant of structure (j):

Structure (j)

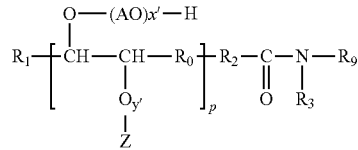

wherein p is 1-3; $R_0$ is nothing or C1-C6 alkylene, preferably nothing or C1 alkylene; $R_1$ and $R_2$ each independently are C1-C18, preferably C1-C14 hydrocarbons, saturated or unsaturated, linear or branched alkyl or alkylene groups so that the total hydrocarbon chain length is C14 to C22, preferably C16-C18; A is a C2-C3 alkylene; x' is 0-100, preferably 1-100, more preferably 1-50, even more preferably 5-20; y' is 0 or 1; Z is a H (hydrogen) when y'=0, a C1-C22 alkyl when y'=1, or a polyalkylene oxide $(A'O)_{w'}H$ when y'=1 where A' is a C2-C3 alkylene and w' is 0-100, preferably 1-50, more preferably 5-20; $R_3$ and $R_9$ each is H, $CH_3$, or $(A'''O)_{w''}H$ where A''' is a C2-C3 alkylene and w''=1-100, preferably 1-50, more preferably 5-20.

The suitable agricultural chemicals include pesticides and growth regulators. The preferred pesticide is an insecticide or herbicide. The preferred herbicide is glyphosate, dicamba, 2,4-D, and glufosinate. The most preferred herbicide is glyphosate. When used in agricultural application, the nitrogen containing surfactant of structure (h), (i), or (j), may be present in the agricultural composition at a level of more than about 0.001 wt %. In one embodiment, the surfactant is present in the composition at a level of more than about 1 wt %; in another embodiment, more than about 10 wt %; in yet another embodiment, more than about 30 wt %; in a further embodiment, more than about 50 wt %. They are particularly useful in agricultural formulations as an adjuvant, a wetting agent, an emulsifier, a solvent, an animal feed additive, and/or a drift control agent.

The present invention is also directed to a method of making a nitrogen containing surfactant of Structure (h). The method comprises the steps of reacting unsaturated fatty acid with ammonium to produce a fatty nitrile; epoxidizing the fatty nitrile; opening the ring of the epoxidized fatty amine to produce a nitrile with di-pendant groups; alkoxylating the nitrile with di-pendant groups; optionally further alkoxylating the alkoxylated nitrile with di-pendant groups; and reducing the alkoxylated nitrile with di-pendant groups.

The present invention is also directed to a method of making a nitrogen containing surfactant of Structure (i). The method comprises the steps of alkoxylating fatty acid, fatty ester, or triglyceride with pendant hydroxyl groups to obtain an alkoxylated product; optionally further alkoxylating the alkoxylated product; and reacting the alkoxylated product with an amine or a polyamine.

The alkoxylation up to 7 or fewer polyalkylene oxide group may be done with a Lewis acid catalyst, such as $BF_3$, on the fatty acid, fatty ester, triglycerides with at least one pendant OH group. Further alkoxylation, however, should be done with an alkaline catalyst, e.g., KOH.

The present invention will now be illustrated by the following non-limiting examples.

Example 1—Ethoxylation of Castor Oil (CO) with 9 EO (ECO9) Made with BF3 Catalyst Castor oil (4040 g) was charged to a clean, dry 2-gallon pressure reactor, heated to 125° C. and dehydrated by nitrogen sparge for a 3-hr period (withdrew 28 g sample to check moisture and, $H_2O$=0.03 wt %), cooled to 60° C. and catalyzed by the addition of 152 g of $BF_3$:$Et_2O$. The mixture was then purged with nitrogen and heated to 95° C. Ethylene Oxide (EO) (1671 g) was added over a 64-min period at 110° C., digested at 110° C. for a 71-min period, cooled to <60° C. and left overnight. The product is ECO9 (each of the three pendant OH groups on the hydrocarbon chain has ~3EO). The next day a portion of the CO+9EO (1838 g) was removed for further derivation.

Example 2—Ethoxylation of Castor Oil with 15 EO (ECO15) Made with BF3 Catalyst

The remaining ECO9 (3845 g) was heated to 95° C., additional EO was added (755 g) at 105-110° C. over a 30-min period, digested at 105-110° C. for a 90-min period, purged and cooled to <60° C. The product is ECO15 (each of the three pendant OH groups on the hydrocarbon chain has ~5EO). A portion of the CO+15EO (2005 g) was removed for further derivation. The EO number on each pendant OH group is about 5 because majority of EO is added to the pendant OH groups and only minor amount of EO is inserted into the ester groups.

Example 3—Ethoxylation of Castor Oil with 24 EO (ECO24) Made with BF3 and KOH Catalyst To the remaining ECO15 (2595 g), in example 2, KOH (20%) in methanol (50 g) was added to neutralize the $BF_3$ and catalyzed the remaining reactions. The mixture was then heated to 135° C. and methanol removed by nitrogen sparge over a 2-hr period. After removal of methanol, EO was added (660 g) over a 120-min period at 140-145° C. and digested at 145° C. for a 105-min period, cooled to <60° C. and a portion of the CO+24EO (ECO24) removed (1331 g) for further derivation.

Example 4—Ethoxylation of Castor Oil with 30 EO (ECO30) Made with BF3 and KOH Catalyst The remaining ECO24 (1924 g) was heated to 135° C. the next day, EO added (300 g) over a 40-min period at 140-145° C., digested at 140-145° C. for a 180-min period, cooled to <60° C. and a portion of the CO+30EO (ECO30) was discharged (1045 g) for further derivation.

Example 5—Ethoxylation of Castor Oil with 45 EO (ECO45) Made with BF3 and KOH Catalyst The remaining ECO30 (1179 g) was heated to 135° C. the next day, EO added (360 g) over a 75-min period at 140-145° C., digested at 140-145° C. for a 180-min period, cooled to <60° C. and the reactor contents discharged (1299 g ECO45).

TABLE 1

Analysis of Castor oil ethoxylates in Examples 1 to 5

| Example # | Sample | Target EO# | Ethoxylation technology | SAP# Corrected | EO# by SAP# |
|---|---|---|---|---|---|
| 1 | ECO9 | 9 EO | BF3 | 130.16 | 8.1 |
| 2 | ECO15 | 15 EO | BF3 | 107.02 | 14.4 |
| 3 | ECO24 | 24 EO | BF3 + KOH (Hybrid) | 81.74 | 25.5 |
| 4 | ECO30 | 30 EO | BF3 + KOH (Hybrid) | 68.44 | 34.6 |
| 5 | ECO45 | 45 EO | BF3 + KOH (Hybrid) | 57.35 | 45.4 |

For example 3, 4 and 5 using KOH as catalyst, the additional EO will be both attached to the pendant ethoxylated groups and inserted to the ester groups. Thus the EO number on each OH group is estimated to be about 6.5, 7.5 and 10 respectively, assuming similar reactivity for attachment and insertion.

Example 6—Castor Oil-12EO Made with a Conventional Catalyst KOH at High Temperature The same one-gallon alkoxylation reactor was used for the reaction. Castor oil (1200 g) and potassium hydroxide 45% liquid (10.5 g) were charged to the reactor and dehydrated at 140° C. for 45 minutes under nitrogen purging to reduce its moisture content to less than 0.10 wt %. The temperature was raised to 160° C., then ethylene oxide (850 g) was charged to the reactor over 90 minutes. During the EO addition, the temperature was maintained at 160-175° C. and pressure at less than 60 psig. Upon the completion of the EO addition, the product mixture was digested for 2 hours at 160-170° C., then purged with nitrogen and cooled to 60° C. Acetic acid (5.0 g) was then charged to the reactor to neutralize the catalyst. The product mixture then discharged. About 1950 g of the ethoxylated product were collected.

The resulting castor oil-12EO is a clear, viscous liquid at room temperature. The result of the hydroxyl number analysis confirms that it is a 14.4EO adduct of castor oil. The result of NMR analysis confirms that both EO insertion at the ester groups and the EO attachment at the hydroxyl groups occurred during the ethoxylation, however almost all of the EO was inserted at the ester groups and only a minute amount of EO was attached at the hydroxyl groups.

Example 7—Castor Oil-12EO Made with a Conventional Catalyst KOH at Low Temperature The experiment in Example 2 was repeated; however, the ethoxylation was done at the low temperature utilized in the first experiment (100-120° C.). Initially, the ethoxylation reaction occurred, but it stalled after the first 200 g of the total 850 g of EO were charged to the reactor, and the experiment had to be aborted. The result of this experiment indicates that, when the regular KOH-catalyzed process is used for ethoxylation of castor oil, the reaction has to be done at high temperature, and the EO insertion to the ester group on the chain is not avoidable.

Examples 8—Amidoamine (APA) of Castor Oil (CO-APA)

Castor oil (CO, 495 g) and Dimethylamino propylamine (DMAPA, 311 g) were charged to a clean, 2-quart pressure reactor in a 6:1 DMAPA:CO molar ratio. Excess DMAPA is used to ensure high degree of conversion. The mixture was purged free of air with nitrogen, pressurized to 20 psig and heated to 160-175° C. for 4-12 hrs. The extent of transamidization was monitored by the disappearance of the ester peak (1740-1750 cm$^{-1}$) using FTIR analysis. Once the ester content was ~5-10% (by peak intensity), the material was cooled and discharged.

CO-APA was then transferred to a clean, dry 2-L flask equipped with mechanical stirrer, Dean-Stark trap, condenser, thermocouple, and nitrogen sparge line. The product was heated to 155° C. with a nitrogen sparge of 1.0 LPM to remove the excess DMAPA from the transamidization. DMAPA removal was considered complete when TAV was stable and approximately equal to the theoretical TAV.

This sample belongs to structure (i) where y' is 0, Z is a H (hydrogen), q=1, x' is zero, $R_3$=H, $R_5$ and $R_7$=CH$_3$, $R_8$=propylene, $R_9$=nothing, and e=0.

Example 9—Amidoamine (APA) of ECO15 (ECO15-APA)

ECO15 (585 g), from example 2 and DMAPA (220 g) were charged to a clean, 2-quart pressure reactor in a 6:1 DMAPA:/ECO molar ratio. Excess DMAPA is used to ensure high degree of conversion. The mixture was purged free of air with nitrogen, pressurized to 20 psig and heated to 160-175° C. for 4-12 hrs. The extent of transamidization was monitored by the disappearance of the ester peak (1740-1750 cm$^{-1}$) using FTIR analysis. Once the ester content was ~5-10% (by peak intensity), the material was cooled and discharged.

ECO15-APA was then transferred to a clean, dry 2-L flask equipped with mechanical stirrer, Dean-Stark trap, condenser, thermocouple, and nitrogen sparge line. The product was heated to 155° C. with a nitrogen sparge of 1.0 LPM to remove the excess DMAPA from the transamidization. DMAPA removal was considered complete when TAV was stable and approximately equal to the theoretical TAV.

This sample belongs to structure (i) where y' is 0, Z is a H (hydrogen), q=1, x' is about 5, $R_3$=H, $R_5$ and $R_7$=CH$_3$, $R_8$=propylene, $R_9$=nothing, and e=0.

Examples 10—Amidoamine (APA) of ECO45 (ECO45-APA)

ECO45 (666 g), from example 5 and DMAPA (169 g) were charged to a clean, 2-quart pressure reactor in a 6:1 DMAPA:/ECO molar ratio. Excess DMAPA is used to ensure high degree of conversion. The mixture was purged free of air with nitrogen, pressurized to 20 psig and heated to 160-175° C. for 4-12 hrs. The extent of transamidization was monitored by the disappearance of the ester peak (1740-1750 cm$^{-1}$) using FTIR analysis. Once the ester content was ~5-10% (by peak intensity), the material was cooled and discharged.

ECO45-APA was then transferred to a clean, dry 2-L flask equipped with mechanical stirrer, Dean-Stark trap, condenser, thermocouple, and nitrogen sparge line. The product was heated to 155° C. with a nitrogen sparge of 1.0 LPM to remove the excess DMAPA from the transamidization. DMAPA removal was considered complete when TAV was stable and approximately equal to the theoretical TAV.

This sample belongs to structure (i) where y' is 0, Z is a H (hydrogen), q=1, x' is about 10, $R_3$=H, $R_5$ and $R_7$=CH$_3$, $R_8$=propylene, $R_9$=nothing, and e=0.

TABLE 2

Summary of material balance and experimental condition in example 8, 9 and 10

| | Example # | | |
|---|---|---|---|
| | 8 | 9 | 10 |
| Samples | CO-APA | ECO15-APA | ECO45-APA |
| Castor oil or ECOx, g | 495 | 585 | 666 |
| DMAPA, g | 311 | 220 | 169 |
| Temperature, ° C. | 160 | 160 | 175 |
| Reaction time, hrs | 3 | 5.5 | 12 |
| % Conversion | 98.5 | 96.7 | 92.7 |
| molar ratio | 5.8 | 6.0 | 7.3 |
| product, g | 715 | 717 | 720 |

TABLE 3

Summary of DMAPA stripping condition final analysis of the samples in example 8, 9 and 10

|  | Example # | | |
|---|---|---|---|
|  | 8 | 9 | 10 |
| Samples | CO-APA | ECO15-APA | ECO45-APA |
| CO/ECOx APA, g | 698 | 700 | 706 |
| DMAPA removed, g | (110) | (78) | (58) |
| Temperature, C. | 155 | 155 | 175 |
| Stripping time, hrs | 6 | 3.75 | 5.5 |
| Nitrogen, LPM | 1 | 1 | 1 |
| Final TAV, me/g | 2.47 | 1.61 | 0.84 |
| Theo TAV, me/g | 2.49 | 1.61 | 0.94 |
| product, g | 554 | 597 | 634 |

Example 11—Amidoamine (APA) Oxides of CO-APA (CO-APA-Ox)

168 gm of the CO-APA (from example 8) was charged to a 500 ml 5-neck flask (closed system) equipped with a stirrer and temperature controller. While mixing, the temperature was raised to 60° C. Then 42 gm of 35% hydrogen peroxide was charged in 10 equal portions over a 1-hour period. The heating mantle was raised/lowered in order to control the exotherm to between 68-72° C. throughout the addition. After all the peroxide was charged, the flask contents were digested for 4 hours at 70-72° C. After the 4-hour digestion period, peroxide was 0.03% and an additional 2 grams of 50% peroxide was added, mixed for 15 minutes, and the vented flask placed into a 60° C. oven to digest overnight. The next day, the product was sampled for analysis and then discharged into 8-ounce bottles.

This sample belongs to structure (i) where y' is 0, Z is a H (hydrogen), q=1, x' is zero, $R_3$=H, $R_5$ and $R_7$=$CH_3$, $R_8$=propylene, $R_9$ is O (oxygen), and e=0.

Example 12—Amidoamine (APA) Oxide of ECO15-APA (ECO15-APA-Ox)

181 gm of the ECO15-APA (from example 9) was charged to a 500 ml 5-neck flask (closed system) equipped with a stirrer and temperature controller. While mixing, the temperature was raised to 60° C. Then 30 gm of 35% hydrogen peroxide was charged in 10 equal portions over a 1-hour period. The heating mantle was raised/lowered in order to control the exotherm to between 68-72° C. throughout the addition. After all the peroxide was charged, the flask contents were digested for 4 hours at 70-72° C. After the 4-hour digestion period, peroxide was 0.03% and an additional 2 grams of 50% peroxide was added, mixed for 15 minutes, and the vented flask placed into a 60° C. oven to digest overnight. The next day, the product was sampled for analysis and then discharged into 8-ounce bottles.

This sample belongs to structure (i) where y' is 0, Z is a H (hydrogen), q=1, x' is ~5, $R_3$=H, $R_5$ and $R_7$=$CH_3$, $R_8$=propylene, $R_9$ is O (oxygen), and e=0.

Example 13—Amidoamine (APA) Oxide of ECO45-APA (ECO45-APA-Ox)

138 gm of the ECO45-APA (from example 10) was charged to a 500 ml 5-neck flask (closed system) equipped with a stirrer and temperature controller. While mixing, the temperature was raised to 60° C. Then 12 gm of 35% hydrogen peroxide was charged in 10 equal portions over a 1-hour period. The heating mantle was raised/lowered in order to control the exotherm to between 68-72° C. throughout the addition. After all the peroxide was charged, the flask contents were digested for 4 hours at 70-72° C. 3. After the 4-hour digestion period, peroxide was 0.03% and an additional 2 grams of 50% peroxide was added, mixed for 15 minutes, and the vented flask placed into a 60° C. oven to digest overnight. The next day, the product was sampled for analysis and then discharged into 8-ounce bottles.

This sample belongs to structure (i) where y' is 0, Z is a H (hydrogen), q=1, x' is about 10, $R_3$=H, $R_5$ and $R_7$=$CH_3$, $R_8$=propylene, $R_9$ is O (oxygen), and e=0.

TABLE 4

Final analysis of amine oxide samples in examples 11, 12 and 13

|  | Example # | | |
|---|---|---|---|
|  | 11 | 12 | 13 |
| Samples | CO-APA-Ox | ECO15-APA-Ox | ECO45-APA-Ox |
| Appearance @ 77° F. | Gel | Clear liquid | Clear liquid |
| Total base, me/g | 1.949 | 1.355 | 0.7516 |
| Amine oxide, me/g | 1.938 | 1.344 | 0.7218 |
| Free amine, me/g | 0.011 | 0.011 | 0.0298 |
| pH (%5 Aq.) | 6.4 | 6 | 5.7 |
| $H_2O_2$, wt % | 0.24 | 0.12 | 0.38 |

Example 14—Amidoamine (APA) Betaine of CO-APA (CO-APA-Bet)

The betaine was synthesized with a 1.3:1.0 molar ratio of sodium monochloroacetate (SMCA) to CO-APA (from example 8). The TAV (perchloric acid titration) was used to calculate the equivalent weight of the APA, which was charged to a clean 500-mL round bottom equipped with mechanical stirrer and thermocouple, heated to 50° C. and SMCA added in 4 equal portions. Upon addition of all required SMCA, the mixture was heated to 90° C. and digested for 4 to 5 hrs.

This sample belongs to structure (i) where y' is 0, Z is a H (hydrogen), q=1, x' is zero, $R_3$=H, $R_5$ and $R_7$=$CH_3$, $R_8$=propylene, $R_9$ is $CH_2$—COO, and e=0.

Example 15—Amidoamine (APA) Betaine of ECO15-APA (ECO15-APA-Bet)

The betaine was synthesized with a 1.3:1.0 molar ratio of sodium monochloroacetate (SMCA) to ECO9-APA (from example 9). The TAV (perchloric acid titration) was used to calculate the equivalent weight of the APA, which was charged to a clean 500-mL round bottom equipped with mechanical stirrer and thermocouple, heated to 50° C. and SMCA added in 4 equal portions. Upon addition of all required SMCA, the mixture was heated to 90° C. and digested for 4 to 5 hrs.

This sample belongs to structure (i) where y' is 0, Z is a H (hydrogen), q=1, x' is ~5, $R_3$=H, $R_5$ and $R_7$=$CH_3$, $R_8$=propylene, $R_9$ is $CH_2$—COO, and e=0.

Example 16—Amidoamine (APA) Betaine of ECO45-APA (ECO45-APA-Bet)

The betaine was synthesized with a 1.3:1.0 molar ratio of sodium monochloroacetate (SMCA) to ECO45-APA (from example 10). The TAV (perchloric acid titration) was used to calculate the equivalent weight of the APA, which was charged to a clean 500-mL round bottom equipped with mechanical stirrer and thermocouple, heated to 50° C. and SMCA added in 4 equal portions. Upon addition of all required SMCA, the mixture was heated to 90° C. and digested for 4 to 5 hrs.

This sample belongs to structure (i) where y' is 0, Z is a H (hydrogen), q=1, x' is about 10, $R_3$=H, $R_5$ and $R_7$=$CH_3$, $R_8$=propylene, $R_9$ is $CH_2$—COO, and e=0.

TABLE 5

Material balance and reaction times for example 14, 15 and 16

| Example #'s | Sample | CO-APA or ECO-APA (g) | SMCA (g) | Digestion Time (hrs) |
|---|---|---|---|---|
| 14 | CO-APA-Bet | 109.5 | 40.5 | 4.5 |
| 15 | ECO15-APA-Bet | 168 | 41 | 5 |
| 16 | ECO45-APA-Bet | 186.3 | 23.7 | 4 |

Each synthesized betaine in example 14, 15 and 16 was then diluted with isopropyl alcohol to a total weight of 400 g and centrifuged in order separate a majority of the sodium chloride. The top betaine layer was then decanted off and residual IPA removed by nitrogen sparge at 100-110° C.

TABLE 6

Summary of the composition of the final samples.

| Example # | Sample | NaCl (wt. %) | Free amine (wt. %) | Betaine (wt. %) |
|---|---|---|---|---|
| 14 | CO-APA-Bet | 2.21 | 1.1 | 84.4 |
| 15 | ECO15 APA Bet | 2.2 | 1.68 | 77.9 |
| 16 | ECO45-APA-Bet | 1.41 | 3.42 | 85 |

Example 17—Methyl Chloride Quaternary of CO-APA (CO-APA-MeQ)

170 g of CO-APA (from example 8) was placed in a 600-mL autoclave together with 10 wt % propylene glycol and 2 wt % $NaHCO_3$. The materials were then purged with nitrogen 3 times and heated to 95°. Methyl chloride feed, 9.3 g (20 mol % excess) entered in ~7 minutes and the digesting time was 6-7 hours to achieve low free amine.

This sample belongs to structure (i) where y' is 0, Z is a H (hydrogen), q=1, x' is zero, $R_3$=H, $R_5$ and $R_7$=$CH_3$, $R_8$=propylene, $R_9$ is $CH_3$, e=1, and X=Cl (chloride).

Example 18—Methyl Chloride Quaternary of ECO15-APA (ECO15-APA-MeQ)

175 g of ECO15-APA (from example 9) was placed in a 600-mL autoclave together with 10 wt % propylene glycol and 2 wt % $NaHCO_3$ (4.2 g). The materials were then purged with nitrogen 3 times and heated to 95°. Methyl chloride feed, 29 g entered in ~7 minutes and the digesting time was 6-7 hours to achieve low free amine.

This sample belongs to structure (i) where y' is 0, Z is a H (hydrogen), q=1, x' is ~5, $R_3$=H, $R_5$ and $R_7$=$CH_3$, R8=propylene, $R_9$ is $CH_3$, e=1, and X=Cl (chloride).

Example 19—Methyl Chloride Quaternary of ECO-APA45 (ECO45-APA-MeQ)

170 g of ECO45-APA (from example 10) was placed in a 600-mL autoclave together with 10 wt % propylene glycol and 2 wt % $NaHCO_3$. The materials were then purged with nitrogen 3 times and heated to 95°. Methyl chloride feed, 9.3 g (20 mol % excess) entered in ~7 minutes and the digesting time was 6-7 hours to achieve low free amine.

This sample belongs to structure (i) where y' is 0, Z is a H (hydrogen), q=1, x' is ~10, R3=H, R5 and R7=$CH_3$, R8=propylene, R9 is $CH_3$, e=1, and X=Cl (chloride).

TABLE 7

Analysis of samples in example 17, 18 and 19

| | Example # | | |
|---|---|---|---|
| | 17 | 18 | 19 |
| Sample | CO-APA-MeQ | ECO15-APA-MeQ | ECO45-APA-MeQ |
| Solvent | PG | PG | No |
| Sodium Bicarbonate | yes | yes | No |
| Free amine, meq/g | 0.024 | 0.029 | 0.004 |
| Free amine, wt % | 1 | 1.5 | 0.5 |
| Amine hydrochloride, meq/g | 0.006 | 0.005 | 0.035 |
| Amine hydrochloride, wt % | 0.3 | 0.3 | 4.1 |
| Quaternary, meq/g | 1.914 | 1.526 | 0.815 |
| Quaternary, wt % | 88.1 | 89.3 | 96.7 |
| Total activity, meq/g | 1.945 | 1.559 | 0.854 |
| NE of free amine | 410 | 535 | 1136 |
| NE of amine hydrochloride | 446 | 571 | 1172 |
| NE of quat | 461 | 586 | 1187 |

Example 20—Methyl Chloride Quaternary of Ricinoleic Acid APA

This reaction obtains the same desired product as in example 17 except here it started with a fatty acid rather than an oil.

Step 1: To a 2 L autoclave was added the 300 g (0.96 mole) ricinoleic acid and 100 g (2 mol % excess) of DMAPA. The reactor was sealed and purged with nitrogen. The outlet was then closed and the reactor was heated to 185° C. and allowed to react. After several hours samples were taken to monitor free fatty acid content via KOH/MeOH titration. Once the free fatty acid was less than 2 wt % the reactor was depressurized and stripped with a nitrogen sparge (0.5 slm) to remove water for 5 hours. The material was removed from the autoclave.

Step 2: To a 120 mL Fisher-Porter bottle was added 50 g of the Ricinoleic acid APA and sealed under nitrogen with stirring. The reactor was heated to 90° C. and purged with nitrogen. The reactor was pressurized to 50 psig with $N_2$ and leaked tested for 15 minutes.

Step 3: If no leaks were detected, the reactor was depressurized and setup for MeCl addition. MeCl was then added to the reactor and allowed to react. The reaction exothermed to 125° C. and the heating bath was removed to cool the reaction down ~90° C. The mixture went cloudy and thickened upon addition of MeCl. After the reaction temperature cooled to 90° C. more MeCl was added and allowed to react. The viscosities of the quats were evaluated visually and the results are summarized in Table 8. Once all of the MeCl was added the reaction was allowed to digest for 30 minutes. The reactor was removed from the heating bath and the material from the bottle and cooled to room temperature. The material was flaked for analysis.

This sample belongs to structure (i) where y' is 0, Z is a H (hydrogen), q=1, x' is zero, $R_3$=H, $R_5$ and $R_7$=$CH_3$, $R_8$=propylene, $R_9$ is $CH_3$, e=1, and X=Cl (chloride).

In example 20, ethylene (or propylene) oxide can be added after Step 2 using well-known alkaline alkoxylation process. The sample obtained belongs to structure (i) where y' is 0, Z is a H (hydrogen), q=1, x' is >0 depending on how many EO is added, $R_3$=H, $R_5$ and $R_7$=$CH_3$, $R_8$=propylene, $R_9$ is $CH_3$, e=1, and X=Cl (chloride).

TABLE 8

Wet analysis of example 20

| | |
|---|---|
| Ricinoleic APA Quat-Activity (meg/g) | 1.997 |
| Ricinoleic APA Quat-NE (g/eq) | 500.8 |
| Ricinoleic APA Quat-Free Amine (meg/g) | 0.007 |
| Ricinoleic APA Quat-Amine Salt (meg/g) | 0.004 |

Example 21 and 22—Amidoamine (APA) of Hydroxylated Soybean Oil (HSO)

Hydroxylated soybean oil (HSO—trade name Agrol 5.6) was obtained from BioBased Technologies. Reactions were performed in a 3 liter 4-neck flask equipped with a stir bar, gas adapter, short vigeraux column, condensor, thermowell, and thermocouple. 728 gm (2.11 OH equivalents) HSO, and 254 gm (2.49 moles) DMAPA were added and heated to 220-240° C. Samples were taken periodically and monitored by FTIR for amide at 1649 $cm^{-1}$ and ester at 1738 $cm^{-1}$. When consecutive samples showed very little change in amide/ester 458 gm was removed and the remaining contents sparged 1 hour at 80° C. This was collected as Example 21 (HSO-APA-1), 476 gm. The previously noted 458 gm was returned to the flask and 24.8 gm, 0.24 moles, more DMAPA was added. And heating continued at 220° C. for 1 hour. The reactor was cooled to 85° C. and sparged for 2 hours. 487 gm of product Example 22 (HSO-APA-2) was collected, along with 4.0 gm distillate, presumably DMAPA. Analysis of Example 21 and 22 are provided below

TABLE 9

Analysis of samples in Example 21 and 22

| | Example # | |
|---|---|---|
| | 21 | 22 |
| Sample | HSO-APA-1 | HSO-APA-2 |
| Form | Gel at r.t. | Gel at r.t. |
| Amine value, mg KOH/g | 144.7 | 159.6 |
| NE, g/eq | 387.5 | 351.4 |
| IR bands, relative intensity | | |
| (1648 $cm^{-1}$ amide I)/ester | 4.11 | 7.83 |
| (1547 $cm^{-1}$ amide II)/ester | 2.52 | 4.67 |
| NMR, mole % | | |
| Ester | 18.5 | 7.7 |
| Amide | 81.1 | 91.2 |
| Amide/Ester, m/m | 4.38 | 11.8 |
| Free DMAPA, wt % by GC | 0.14 | 0.56 |

The samples in example 21 and 22 belongs to structure (i) where y' is 1; Z is a H (hydrogen), q=1, x' is zero, $R_3$=H, $R_5$ and $R_7$=$CH_3$, $R_8$=propylene, $R_9$=nothing, and e=0.

Examples 8-22 used DMAPA as the amine for the reactions. It is obvious to a skilled in the art that the same reactions can be carried out to obtain corresponding structures by using another amine using similar reaction conditions.

Example 23—Bioefficacy Enhancing Effect of Nitrogen Containing Castor Oil Derivatives on Wheat A greenhouse trial was conducted by spraying solutions of 300 g ae/HA of IPA-glyphosate on wheat. The glyphosate formulation was based on 360 g/L IPA containing 10% active surfactant. Wheat was used as the "weed" because it germinates smoothly and it is a good species for herbicide study. The untreated check (UTC) was sprayed with only water. Pot 150 was sprayed with glyphosate only solution. Pot 149 was sprayed with glyphosate solution containing tallowamine-15EO (TAE15). TAE15 is the most common surfactant used to enhance glyphosate efficacy.

Plants were sprayed with glyphosate solutions containing surfactant according to the present invention. Table below lists the various surfactants and their corresponding pots. Percent growth control data for 4 weeks after treatment is also shown in this table as well. Percent growth control data was obtained from the fresh weight of these plants. The data clearly indicates glyphosate solutions containing surfactant according to the present invention provides better growth control than glyphosate only, thus acting as an adjuvant. In many cases the adjuvancy is equal to that of TAE15. Pictures of these plants at 4 weeks after treatment are shown in FIG. 1.

TABLE 10

Bioefficacy enhancing effect of novel castor oil ethoxylate derivatives on Wheat

| Pot# | Surfactant | % Growth Control |
|---|---|---|
| 127 | ECO15 | 83 |
| 129 | ECO45 | 80 |
| 130 | CO-APA-Ox | 87 |
| 131 | ECO15-APA-Ox | 84 |
| 133 | ECO45-APA-Ox | 96 |
| 134 | CO-APA-Bet | 93 |
| 136 | ECO15-APA-Bet | 88 |
| 138 | ECO45-APA-Bet | 85 |
| 139 | CO-APA-MeQ | 83 |
| 140 | ECO15-APA-MeQ | 91 |
| 142 | ECO45-APA-MeQ | 90 |
| 149 | TAE15 | 95 |
| 150 | IPA Glyphosate alone | 66 |
| UTC | Water only | 0 |

Comparing the % Growth Control for Pots containing the nitrogen containing surfactants of the present invention (top 11 pots), it can be seen in this greenhouse study that of the nitrogen containing surfactants of the present invention can enhance the bioefficacy of glyphosate (Pot 150).

Example 24—Bioefficacy Enhancing Effect of Nitrogen Containing Hydroxylated Soybean Oil Derivatives on Wheat A separate set of test was conducted for these surfactants. The condition and treatment of example 24 was identical to example 23. Table below shows the % growth control data for 4 weeks after treatment provided by these surfactants together with data for Tallow amine ethoxylate (with 15

EO), IPA glyphosate alone and UTC (as described above). In this case % growth control is a qualitative data obtained by visual inspection of the plants. The data clearly indicates glyphosate solutions containing surfactant according to the present invention provides enhanced growth control than glyphosate only, thus acting as an adjuvant.

TABLE 11

Bioefficacy enhancing effect of novel Hydroxylated Soybean oil derivatives on Wheat

| Sample | % Growth Control (qualitative) |
|---|---|
| HSO-APA-1 | 94 |
| HSO-APA-2 | 92 |
| TAE15 | 95 |
| IPA Glyphosate alone | 55 |
| Water only (UTC) | 0 |

Example 25—Bioefficacy Enhancing Effect of Nitrogen Containing Castor Oil Ethoxylate Derivatives on Morningglory The condition and treatment of example 25 was identical to example 23 except that example 25 used morning glory instead of wheat.

The following picture showed the result 4 weeks after treatment (WAT). The result showed that the ranking order of morningglory control was: pot 121, pot 129, pot 120, pot 130, UTC (untreated check). That is, the castor oil-45EO DMAPA (ECO45-APA) showed slightly better control than tallowamine-15EO while castor oil-15EO DMAPA quaternary (ECO15-APA-MeQ) showed similar control as tallowamine-15EO. Pot 130 didn't show much control. The result can be summarized in Table 12.

TABLE 12

Bioefficacy enhancing effect of nitrogen containing castor oil ethoxylate derivatives on morning glory

| | Pot 120 | Pot 121 | Pot 129 (positive control) | Pot 130 | Pot UTC (control) |
|---|---|---|---|---|---|
| Surfactant | Castor oil-15EO DMAPA quat | Castor oil-45EO DMAPA | Tallowamine-15EO | No surfactant | No surfactant |
| Sprayed Glyphosate rate, g ae/HA | 300 | 300 | 300 | 300 | 0 |
| Sprayed Glyphosate ae:surfactant ai | ~3:1 | ~3:1 | 3:1 | No surfactant | No surfactant |
| Morning glory at 4WAT | Some green leaf left | A little green leaf left | A little green leaf left | Healthy morning glory | Healthy morning glory |

We claim:

1. An agricultural composition comprising at least one agricultural chemical and at least one nitrogen containing surfactant composition, wherein the agricultural chemical is an herbicide and the nitrogen containing surfactant composition comprises at least one nitrogen containing surfactant of structure (i):

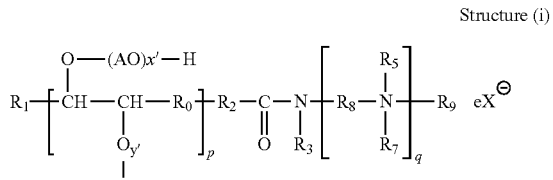

Structure (i)

wherein p is 1-3;

$R_0$ is nothing or C1-C6 alkylene;

$R_1$ and $R_2$ each independently are C1-18 hydrocarbons, saturated or unsaturated, linear or branched alkyl or alkylene groups so that the total hydrocarbon chain length is C14 to C22;

A is a C2-C3 alkylene;

x' is 0-100;

y' is 0 or 1;

Z is a H (hydrogen) when y'=0, a C1-C22 alkyl when y'=1, or a polyalkylene oxide $(A'O)_{w'}H$ when y'=1 where A' is a C2-C3 alkylene and w' is 0-100;

$R_3$ is H, $CH_3$, or $(A'''O)_{w''}H$ where A''' is a C2-C3 alkylene and w''=1-100;

$R_5$, $R_7$, and $R_9$ are the same or different and are selected from nothing, H, $CH_3$, $CH_3CH_2$, $(A''O)_wH$ where A'' is a C2-C3 alkylene and w=1-100, O (oxygen), $CH_2$—COO, $CH_2$—COO$^-$M$^+$, $CH_2$—$CH_2$—COO$^-$M$^+$, $CH_2$—$CH_2$—$CH_2$—$SO_3$, or $CH_2$—CH(OH)—$CH_2$—$SO_3$;

q=1-5;

$R_8$ is C2-C3 alkylene;

X$^-$ is an anion and e is a value that balances the charge in the molecule when N is a quaternary nitrogen; and M$^+$ is a suitable cation; or at least one nitrogen containing surfactant of structure (h):

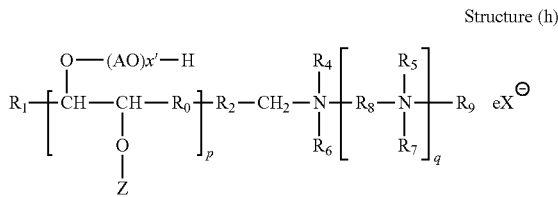

Structure (h)

wherein p is 1-3; $R_0$ is nothing or C1-C6 alkylene; $R_1$ and $R_2$ each independently are C1-C18 hydrocarbons, saturated or unsaturated, linear or branched alkyl or alkylene groups so that the total hydrocarbon chain length is C14 to C22; A is a C2-C3 alkylene; x' is 0-100; Z is C1-C22 alkyl or a polyalkylene oxide $(A'O)_w'H$ where A' is a C2-C3 alkylene and w' is 0-100; $R_4$, $R_5$, $R_6$, $R_7$, and $R_9$ are the same or different and are selected from nothing, H, $CH_3$, $CH_3CH_2$, $(A''O)_wH$ where A'' is a C2-C3 alkylene and w=1-100, O (oxygen), $CH_2$—COO, $CH_2$—$COO^-M^+$, $CH_2$—$CH_2$—$COO^-M^+$, $CH_2$—$CH_2$—$CH_2$—$SO_3$, or $CH_2$—$CH(OH)$—$CH_2$—$SO_3$; q=0-5; $R_8$ is C2-C3 alkylene; X'' is an anion and e is a value that balances the charge in the molecule when N is a quaternary nitrogen; and $M^+$ is a suitable cation; or at least one nitrogen containing surfactant of structure (j):

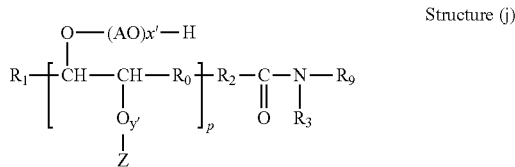

Structure (j)

wherein p is 1-3; $R_0$ is nothing or C1-C6 alkylene; $R_1$ and $R_2$ each independently are C1-C18 hydrocarbons, saturated or unsaturated, linear or branched alkyl or alkylene groups so that the total hydrocarbon chain length is C14 to C22; A is a C2-C3 alkylene; x' is 0-100; y' is 0 or 1; Z is a H (hydrogen) when y'=0, a C1-C22 alkyl when y'=1, or a polyalkylene oxide $(A'O)_w'H$ when y'=1 where A' is a C2-C3 alkylene and w' is 0-100; $R_3$ and $R_9$ each is H, $CH_3$, or $(A'''O)_{w''}H$ where A''' is a C2-C3 alkylene and w''=1-100; wherein the concentration of the at least one nitrogen containing surfactant composition is present in the agricultural composition at a level of greater than 0.001 wt %.

2. An agricultural composition according to claim 1 comprising the nitrogen containing surfactant of structure (i):

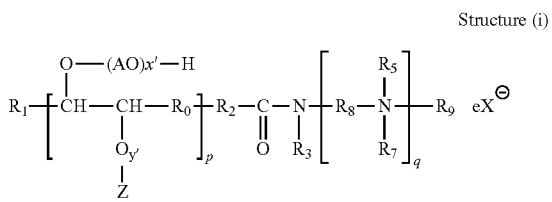

Structure (i)

wherein R3 is H; $R_5$ and $R_7$ are each $CH_3$; $R_9$ is selected from nothing, H, $CH_3$, $CH_3CH_2$, O (oxygen), $CH_2$—COO and $CH_2$—$COO^-M^+$; q=1; and $R_8$ is propylene.

3. An agricultural composition according to claim 1 comprising the nitrogen containing surfactant of structure (i) wherein q=1, $R_3$ is H, $R_8$ is C3 (propylene), $R_5$ and $R_7$ is each $CH_3$, $R_9$ is nothing, and e is zero.

4. An agricultural composition according to claim 1 comprising the nitrogen containing surfactant of structure (i) wherein q=1, $R_3$ is H, $R_8$ is C3 (propylene), $R_5$ and $R_7$ is each $CH_3$, $R_9$ is O (oxygen), and e is zero.

5. An agricultural composition according to claim 1 comprising the nitrogen containing surfactant of structure (i) wherein q=1, $R_3$ is H, $R_8$ is C3 (propylene), $R_5$ and $R_7$ is each $CH_3$, $R_9$ is $CH_2$—COO, and e is zero.

6. An agricultural composition according to claim 1 comprising the nitrogen containing surfactant of structure (i) wherein q=1, $R_3$ is H, $R_8$ is C3 (propylene), $R_5$ and $R_7$ is each $CH_3$, $R_9$ is methyl (or ethyl), e is 1, and X is chloride or sulfate.

7. An agricultural composition according to claim 1 comprising the nitrogen containing surfactant of structure (i) wherein q=1, $R_3$ is H, $R_8$ is C2 (ethylene), $R_5$ is H, $R_7$ is $(A''O)_wH$ where w=1, $R_9$ is nothing, and e is zero.

8. An agricultural composition according to claim 1 comprising the nitrogen containing surfactant of structure (i) wherein q=1, $R_3$ is H or $(A'''O)_{w''}H$ where w''=1-100, $R_8$ is C2 (ethylene), $R_7$ and $R_5$ are each $(A''O)_wH$ where w=1-100; $R_9$ is nothing; and e is zero.

9. An agricultural composition according to claim 1 comprising the nitrogen containing surfactant of structure (i) wherein q=1, $R_3$ is H or $(A'''O)_{w''}H$ where w''=1-100; $R_8$ is C2 (ethylene); $R_7$ and $R_5$ are each $(A''O)_wH$ where w=1-100; $R_9$ is O (oxygen); and e is zero.

10. An agricultural composition according to claim 1 comprising the nitrogen containing surfactant of structure (i) wherein q=1, $R_3$ is H or $(A'''O)_{w''}H$ where w=1-100; $R_8$ is C2 (ethylene); $R_7$ and $R_5$ are each $(A''O)_wH$ where w=1-100; $R_9$ is methyl or ethyl; e is 1; and X is chloride or sulfate.

11. An agricultural composition according to claim 1 comprising the nitrogen containing surfactant of structure (i) wherein q=2; $R_3$ is H or $(A'''O)_{w''}H$ where w=1-100; $R_8$ is C2 (ethylene); $R_5$ is nothing, H, or $(A''O)_wH$ where w=1-100; $R_7$ is H or $(A''O)_wH$ where w=1-100, $R_9$ is nothing, and e is zero.

12. An agricultural composition according to claim 1 comprising the nitrogen containing surfactant of structure (i) wherein q=2; $R_3$ is H or $(A'''O)_{w''}H$ where w''=1-100; $R_8$ is C2 (ethylene); $R_5$ is nothing or O (oxygen); $R_7$ is $(A''O)_wH$ where w=1-100; $R_9$ is nothing or O (oxygen); and e is zero.

13. An agricultural composition according to claim 1 comprising the nitrogen containing surfactant of structure (i) wherein q=2; $R_3$ is H or $(A'''O)_{w''}H$ where w''=1-100; $R_8$ is C2 (ethylene); $R_5$ is nothing or $CH_3$; $R_7$ is $(A''O)_wH$ where w=1-100; $R_9$ is nothing or $CH_3$ or ethyl; e is 1 or >1; and X is chloride or sulfate.

14. An agricultural composition according to claim 1 comprising the nitrogen containing surfactant of structure (h) wherein q=0, $R_4$ and $R_6$ are each methyl, $R_9$ is nothing, and e is zero.

15. An agricultural composition according to claim 1 comprising the nitrogen containing surfactant of structure (h) wherein q=0, $R_4$ and $R_6$ are each methyl, $R_9$ is $CH_2$—COO, and e is zero.

16. An agricultural composition according to claim 1 comprising the nitrogen containing surfactant of structure (h) wherein q=0, $R_4$ and $R_6$ are each methyl, $R_9$ is O (oxygen), and e is zero.

17. An agricultural composition according to claim 1 comprising the nitrogen containing surfactant of structure (h) wherein q=0, $R_4$ and $R_6$ are each methyl, $R_9$ is methyl (or ethyl), e is 1, and X is chloride (or sulfate).

18. An agricultural composition according to claim 1 comprising the nitrogen containing surfactant of structure (h) wherein q=0, $R_4$ and $R_6$ are each $(A''O)_wH$ where w=1-100; $R_9$ is nothing; and e is zero.

19. An agricultural composition according to claim 1 comprising the nitrogen containing surfactant of structure (h) wherein q=0, $R_4$ and $R_6$ are each $(A''O)_wH$ where w=1-100; $R_9$ is O (oxygen); and e is zero.

20. An agricultural composition according to claim 1 comprising the nitrogen containing surfactant of structure (h) wherein q=0, $R_4$ and $R_6$ are each $(A''O)_wH$ where w=1-100; $R_9$ is methyl (or ethyl); e is 1; and X is chloride or sulfate.

21. An agricultural composition according to claim 1 comprising the nitrogen containing surfactant of structure (h) wherein q=0, $R_4$ and $R_6$ are each methyl or $(A''O)_wH$ where w=1, $R_9$ is $CH_2$—COO, and e is zero.

22. The agricultural composition of claim 1 wherein the concentration of the at least one nitrogen containing surfactant is greater than 1 wt %.

23. The agricultural composition of claim 1 wherein the concentration of the at least one nitrogen containing surfactant is greater than 10 wt %.

24. The agricultural composition of claim 1 wherein the concentration of the at least one nitrogen containing surfactant is greater than 30 wt %.

25. The agricultural composition of claim 1 wherein the concentration of the at least one nitrogen containing surfactant is greater than 50 wt %.

26. The agricultural composition of claim 1 wherein the herbicide is glyphosate.

27. The agricultural composition of claim 1 wherein the herbicide is dicamba.

28. The agricultural composition of claim 1 wherein the herbicide is 2,4-D.

29. The agricultural composition of claim 1 wherein the herbicide is glufosinate.

30. The agricultural composition of claim 26 wherein the agricultural composition further comprises a C5-C12 dimethylamidopropylamine.

31. A nitrogen containing surfactant of structure (h):

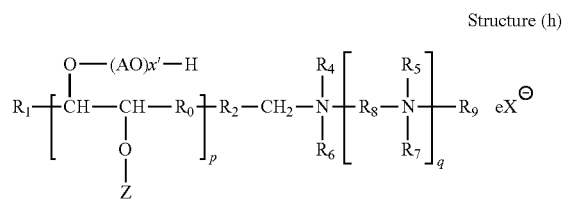

Structure (h)

wherein p is 1-3; $R_0$ is nothing or C1-C6 alkylene; $R_1$ and $R_2$ each independently are C1-C18 hydrocarbons, saturated or unsaturated, linear or branched alkyl or alkylene groups so that the total hydrocarbon chain length is C14 to C22; A is a C2-C3 alkylene; x' is 0-100; Z is C1-C22 alkyl or a polyalkylene oxide $(A'O)_w'H$ where A' is a C2-C3 alkylene and w' is 0-100; $R_4$, $R_5$, $R_6$, $R_7$, and $R_9$ are the same or different and are selected from nothing, H, $CH_3$, $CH_3CH_2$, $(A''O)_wH$ where A'' is a C2-C3 alkylene and w=1-100, O (oxygen), $CH_2$—COO, $CH_2$—COO$^-M^+$, $CH_2$—$CH_2$—COO$^-M^+$, $CH_2$—$CH_2$—$CH_2$—$SO_3$, or $CH_2$—CH(OH)—$CH_2$—$SO_3$; q=0-5; $R_8$ is C2-C3 alkylene; $X^-$ is an anion and e is a value that balances the charge in the molecule when N is a quaternary nitrogen; and $M^+$ is a suitable cation.

32. A method of making a nitrogen containing surfactant of structure (h) as defined in any one of claims 31 and 14-21, the method comprising the steps of:
    reacting unsaturated fatty acid with ammonium to produce a fatty nitrile;
    epoxidizing the fatty nitrile;
    opening the ring of the epoxidized fatty amine to produce a nitrile with di-pendant groups;
    alkoxylating the nitrile with di-pendant groups;
    optionally further alkoxylating the alkoxylated nitrile with di-pendant groups; and
    reducing the alkoxylated nitrile with di-pendant groups.

33. A method of claim 32 wherein the alkoxylation up to 7 or fewer polyalkylene oxide group is done with a Lewis acid catalyst on the fatty acid, fatty ester, triglycerides with at least one pendant OH group.

34. A method of claim 33 wherein the further alkoxylation is done with an alkaline catalyst.

35. A agricultural composition according to claim 1 wherein w' and w'' of structure (j) is 1-50.

36. A agricultural composition according to claim 1 wherein w' and w'' of structure (j) is 5-20.

* * * * *